(12) United States Patent
Afsarifard et al.

(10) Patent No.: US 9,775,780 B2
(45) Date of Patent: Oct. 3, 2017

(54) SMART MEDICATION CONTAINER

(71) Applicant: Kali Care, Inc., Mountain View, CA (US)

(72) Inventors: Navid Nick Afsarifard, Atherton, CA (US); Sina Fateh, Mountain View, CA (US)

(73) Assignee: KALI CARE, INC., Mountain View, CA (US)

( * ) Notice: Subject to any disclaimer, the term of this patent is extended or adjusted under 35 U.S.C. 154(b) by 0 days.

(21) Appl. No.: 15/279,211

(22) Filed: Sep. 28, 2016

(65) Prior Publication Data

US 2017/0095405 A1    Apr. 6, 2017

Related U.S. Application Data

(60) Provisional application No. 62/237,994, filed on Oct. 6, 2015.

(51) Int. Cl.
*A61J 7/04* (2006.01)
*G06F 19/00* (2011.01)

(52) U.S. Cl.
CPC .............. *A61J 7/04* (2013.01); *A61J 7/0418* (2015.05); *A61J 7/0436* (2015.05); *G06F 19/3456* (2013.01); *G06F 19/3462* (2013.01); *A61J 2200/30* (2013.01); *A61J 2200/70* (2013.01); *A61J 2200/72* (2013.01); *A61J 2205/70* (2013.01)

(58) Field of Classification Search
CPC .......... A61J 7/04; A61J 7/0418; A61J 7/0436; G06F 19/3462
See application file for complete search history.

(56) References Cited

U.S. PATENT DOCUMENTS 5,954,225 A * 9/1999 Powe ................... A61J 7/0481
  206/459.1
7,928,835 B1 * 4/2011 Jovanov ............... A61J 7/0481
  340/309.16

(Continued)

OTHER PUBLICATIONS

International Search Report and Written Opinion PCT/US2016/055560 dated Dec. 29, 2016, pp. 1-7.

*Primary Examiner* — Timothy Waggoner
(74) *Attorney, Agent, or Firm* — Perkins Coie LLP (57) ABSTRACT

Various embodiments relate to systems and methods for monitoring adherence to a medication regimen through the use of a smart medication container. The container can include an electronic display that presents relevant information, such as dosage and/or medication information, instructions, user information, messages, notifications, and device information (e.g., battery status, network connectivity status). A pair of conductive elements positioned on either side of the container's opening can be configured to continually measure capacitance in order to identify when contents (e.g., pills) leave the container. More than one pair of conductive elements may be used to improve accuracy and reduce the effects of noise. A processor is able to analyze the capacitance data and determine whether medication has been dispensed from the container and, if so, how much medication was dispensed. A computer system can then compare the results to a planned medication regimen to determine a state of compliance.

17 Claims, 10 Drawing Sheets

(56) References Cited

U.S. PATENT DOCUMENTS

| | | | |
|---|---|---|---|
| 8,600,549 B2* | 12/2013 | Park | A61J 7/0409 |
| | | | 221/122 |
| 9,460,265 B2* | 10/2016 | Burrows | G06F 19/3456 |
| 2006/0124655 A1 | 6/2006 | Ratnakar | |
| 2007/0024465 A1* | 2/2007 | Howell | A61B 5/01 |
| | | | 340/870.01 |
| 2012/0056000 A1* | 3/2012 | Shores | A61J 7/0436 |
| | | | 235/492 |
| 2014/0058561 A1* | 2/2014 | Rothschild | A61J 1/03 |
| | | | 700/244 |
| 2014/0251850 A1 | 9/2014 | Huang et al. | |

\* cited by examiner

SMART MEDICATION CONTAINER

CROSS-REFERENCE TO RELATED APPLICATION(S)

This application claims the benefit of U.S. Provisional Patent Application No. 62/237,994 entitled "SMART MEDICATION CONTAINER," filed on Oct. 6, 2015, which is incorporated by reference herein in its entirety.

FIELD OF THE INVENTION

Various embodiments concern systems and methods for managing administration of medication and monitoring compliance with medication regimens. More specifically, various embodiments relate to intelligent (i.e., "smart") medication containers that are able to determine when medication has been dispensed and thus monitor adherence to a medication regimen.

BACKGROUND

Approximately thirty percent of medication prescriptions are never filled, and nearly fifty percent of medications for chronic diseases (i.e., long-lasting conditions) are not taken as prescribed. This lack of adherence to medication regimens has dramatic effects on the health of individuals and healthcare costs for society as a whole. Non-adherence has been estimated to cost the U.S. health care system $200 billion annually.

Orally-administered medications, such as pills, are often used to treat a variety of ailments, including high cholesterol (e.g., Lipitor®, Crestor®), arthritis (e.g., Humira®) and diabetes (e.g., Januvia®). Many medications are taken orally because they are intended to have a systemic effect, and because of the ease with which they can be administered. Topically-administered medications, such as eye drops, are also often used to treat chronic diseases. However, almost seventy-five percent of patients admit to some form of noncompliant behavior, over thirty percent do not fill their prescriptions, and nearly fifty percent discontinue their prescriptions within six months of being prescribed.

While forgetfulness is one barrier to adherence, it is not the only barrier, Taking the medication at the wrong time, stopping administration of the medication too early, and taking the wrong dose also represent serious barriers to adhering to a medication regimen. Unfortunately, there are no effective systems for managing adherence to a medication regimen, which may be vital to maintaining or improving an individual's health.

BRIEF DESCRIPTION OF THE DRAWINGS

These and other objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

The figures depict various embodiments described throughout the Detailed Description for purposes of illustration only. While specific embodiments have been shown by way of example in the drawings and are described in detail below, the technology is amenable to various modifications and alternative forms. The intention, however, is not to limit the invention to the particular embodiments described. Accordingly, the claimed subject matter is intended to cover all modifications, equivalents, and alternatives falling within the scope of the technology as defined by the appended claims.

DETAILED DESCRIPTION

Various embodiments are described herein that relate to systems and methods for monitoring administration of medication and adherence to a medication regimen. More specifically, various embodiments relate to an intelligent (i.e., "smart") medication container that holds medication, such as pills, and is able to determine when medication is dispensed. A medication regimen is a plan to make a person become or stay healthy by administering medication. A regimen can, for example, identify what medication(s) an individual is to take or have administered, the time and/or frequency that one or more doses of medication are to be administered, the amount or quantity of medication to be administered, a duration of time a medication is to be administered (e.g., start and end times), etc.

There are many reasons why an individual may not adhere to a medication regimen. For example, an individual may simply forget to take the medication, misunderstand the regimen itself, make an error about the amount or quantity of medication to be administered in a single dose, or forget to refill a prescription. Other pressures (e.g., cost) may also play a role in influencing whether an individual complies with the requirements of a regimen.

This lack of adherence can result in severe consequences for a person's health. Oftentimes, numerous people have a vested interest in whether the person adheres to the regimen, such as a relative or medical professional. For example, the child of an elderly parent may wish to know when (or whether) medication is administered to the parent so that the child can determine whether the parent is adhering to a medication regimen. Non-adherence may prompt the child to take action (e.g., identify why medication is not being administered, ensure medication is properly administered in the future).

The smart medication container described herein can include an electronic display that presents relevant information, such as dosage and/or medication information, textual instructions, animations, user information, messages (e.g., text messages delivered via a cloud service), notifications, and device information (e.g., battery status, network connectivity status). As further described below, the contents (e.g., pills) of the container can be determined by measuring the capacitance between two conductive elements positioned on either side of the container's opening. More than one pair of conductive elements may be used if the opening is in the form of a square, hexagon, etc. A processor is able to analyze the capacitance data and determine whether medicine has been dispensed from the container and, if so, how much medication was dispensed. Afterwards, the smart medication container or another computing device (e.g., mobile phone, tablet, computer, server) may be configured to compare the results to a planned medication regimen to determine a state of compliance.

Terminology

Brief definitions of terms, abbreviations, and phrases used throughout this application are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware (or any combination thereof) components. Modules are typically functional components that can generate useful data or other output using specified input(s). A module may or may not be self-contained. An application program (also called an "application") may include one or more modules, or a module can include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, and special significance is not to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

System Topology Overview

Figure 1:
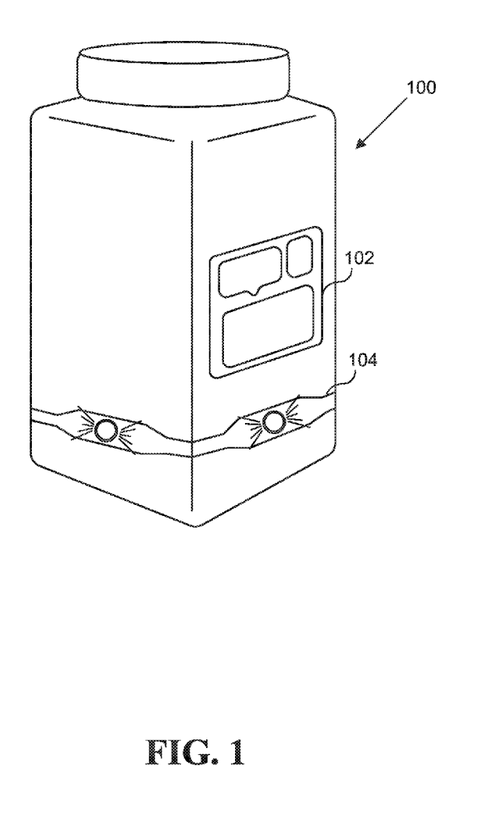
FIGS. 1-3 are perspective views of example smart medication containers according to various embodiments.

FIG. 1 is a perspective view of a smart medication container 100 that includes an electronic display 102 and one or more light sources 104. Generally, the electronic display 102 is a memory display with a persistent (i.e., "always-on") display that consumes minimal power, such as E Ink. However, the electronic display 102 could also be a conventional liquid crystal display (LCD), light-emitting diode (LED) display, etc. In some embodiments, the electronic display 102 is touch-sensitive and provides touch functionality. Touch functionality may allow a user to input messages, answer questions posed by the smart medication container 100, etc.

The electronic display 102 preferably serves as an interactive digital label. For example, the electronic display 102 may allow the user to readily exchange information with a cloud-based service configured to monitor adherence to a medication regimen, medical professionals (e.g., doctors, nurses, pharmacists), medical entities (e.g., hospitals, pharmacies), etc. Information transmitted by the user may include, for example, descriptions of side effects experienced by the user or answers to questions previously posed by a medical professional. The electronic display 102 can be configured to relay automated content and/or allow the user to easily communicate with others across a network. Other information could also be presented on the electronic display 102, such as:

Past, current, and upcoming dosage information;
Instructions regarding how to administer the medication (e.g., textual instructions, animations) and other prescription details (e.g., progress towards completion of the regimen);
Medication name and other pertinent information, including possible side effects, warnings regarding possible interactions with other medications and foods, etc.;
Personal information about the user (e.g., from a user profile);
Messages pushed to the smart medication container (e.g., from the cloud-based service);
Information regarding remaining contents of the container;
Notifications regarding prescription refills; and Device information (e.g., battery status, network connectivity status).

The smart medication container 100 can also include one or more light sources 104 that are able to provide visual reminders to administer medication. In some embodiments the light source(s) 104 are multicolor LEDs that visually convey information to the user. For example, the light source(s) 104 may pulse red when the user is due to administer medication, green when medication has been properly administered, and blue when the smart medication container 100 is establishing a network connection or receiving/transmitting information. Generally, the light source(s) 104 are coupled to each side of the smart medication container 100 and, therefore, are visible on all sides. However, in some embodiments the light source(s) 104 may only be visible on some subset of the sides.

Figure 2:
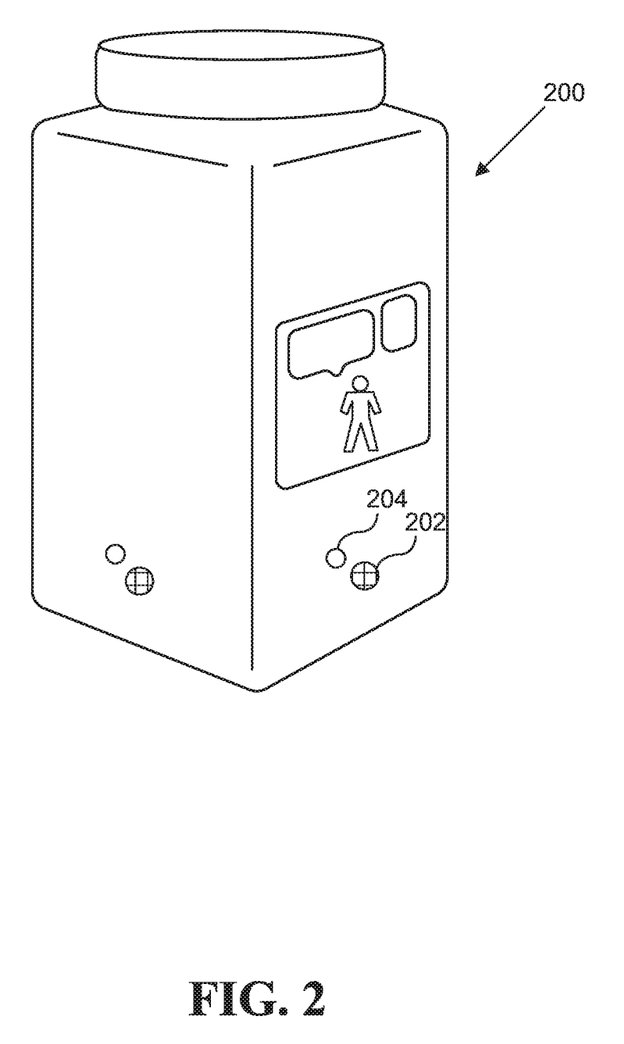

FIG. 2 is a perspective view of a smart medication container 200 that includes at least one audio sensor 202 and at least one audio speaker 204. The audio speaker 204 is configured to generate tones, voice prompts, custom sounds, or some combination thereof. For example, these sounds may provide an audible reminder that medication should be administered or instructions regarding proper administration. The audio sensor 202 (e.g., microphone), meanwhile, is able to record sound produced by or near the smart medication container 200. Consequently, the user may be able to audibly communicate with a family member, medical professional, etc., while administering the medication. As further described below with respect to FIG. 5, the audio sensor 202 may capture and record sounds produced by the user, and reduce or substantially eliminate other ambient sounds. Together, the audio sensor 202 and audio speaker 204 can be used to enable real-time (or near real-time), two-way voice communication. Such communications may correspond to information or animations presented on the electronic display.

Figure 3:
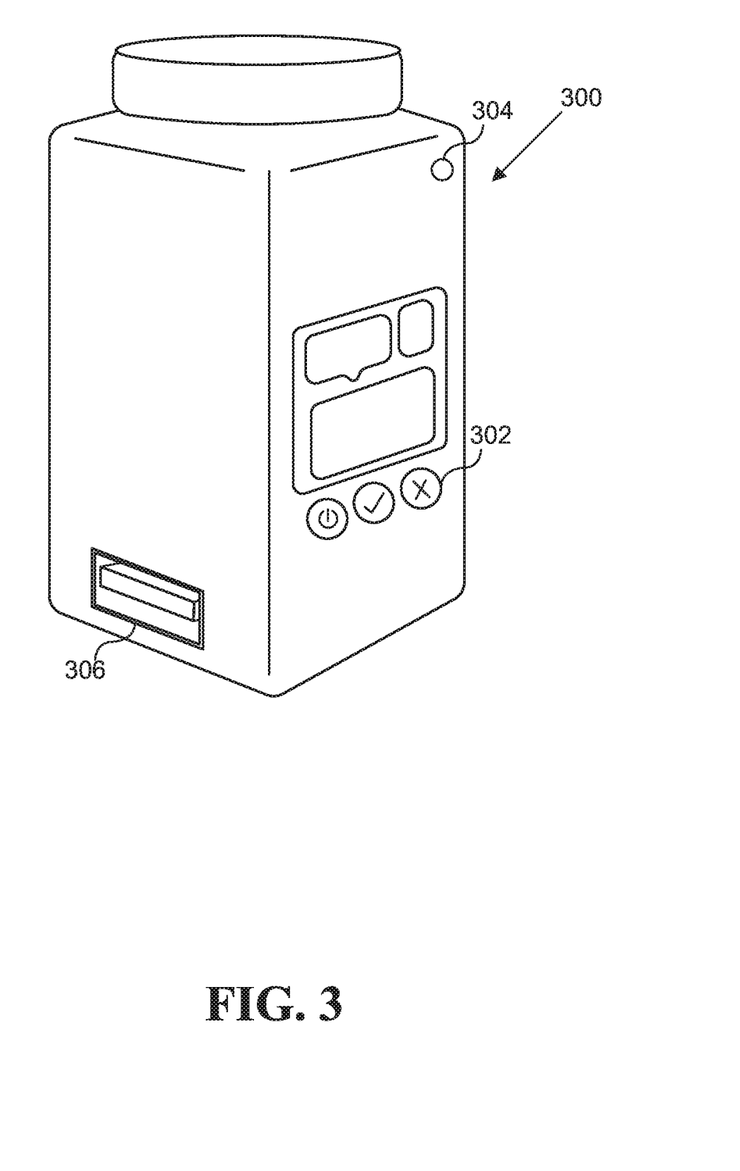

FIG. 3 is a perspective view of a smart medication container 300 that includes one or more user inputs 302, one or more sensors 304 configured to track ambient conditions (e.g., temperature, humidity, ambient or "available" light), and a power supply connection 306. Here, the user input(s) 302 are illustrated as buttons; however, input could also be received by a touch-sensitive electronic display, a microphone and processor employing voice recognition techniques, a camera and processor employing gesture recognition techniques, etc. Input(s) could also be provided using another computing device, such as a mobile phone or laptop, that is paired with (i.e., communicatively coupled to) the smart medication container 300.

In some embodiments, the smart medication container 300 includes sensor(s) 304 that is/are able to monitor various aspects of the user's local environment. For example, the sensor(s) 304 may include a camera configured to capture the user's interactions with the local environment, a light sensor configured to track ambient light levels, a humidity sensor configured to monitor local humidity, a thermometer configured to monitor local temperature, etc. These environmental factors (and others) may have an effect on the medication itself or on the intake of the medication. For example, changes in humidity and/or temperature may affect the user's ability to metabolize the medication. Each of the sensor(s) 304 may be configured to measure values for the local environment, for the inside of the container (i.e., where medication is stored), or both.

A power supply connection 306 may also be coupled to, or configured within, the smart medication container 300. Here, the smart medication container 300 is illustrated as having a standard Universal Serial Bus (USB) port through which power can be provided. Alternatively or additionally, other ports may be used that support micro-USB, Lightning, SATA cables, unique proprietary connectors, etc. The smart medication container 300 could also include a battery compartment within which one or more batteries (e.g., AA, AAA, lithium button) are stored. Further yet, the smart medication container 300 may include power supply connection(s) 306 along the sides and/or bottom of the container that allow the smart medication container 300 to be placed within a charging station for charging. In some embodiments, the smart medication container 300 is charged using inductive charging. More specifically, the smart medication container 300 may be charged via resonant inductive coupling by placing the container 300 on top of a power transmission pad. Those smart medication containers 300 configured for low power inductive transfer of power typically do not have an external power supply connection 306. However, in some instances, it may be preferable for the smart medication container 300 to be chargeable in numerous ways (e.g., via a USB port and via wireless charging in conformance with the Qi standard).

Figure 4A:
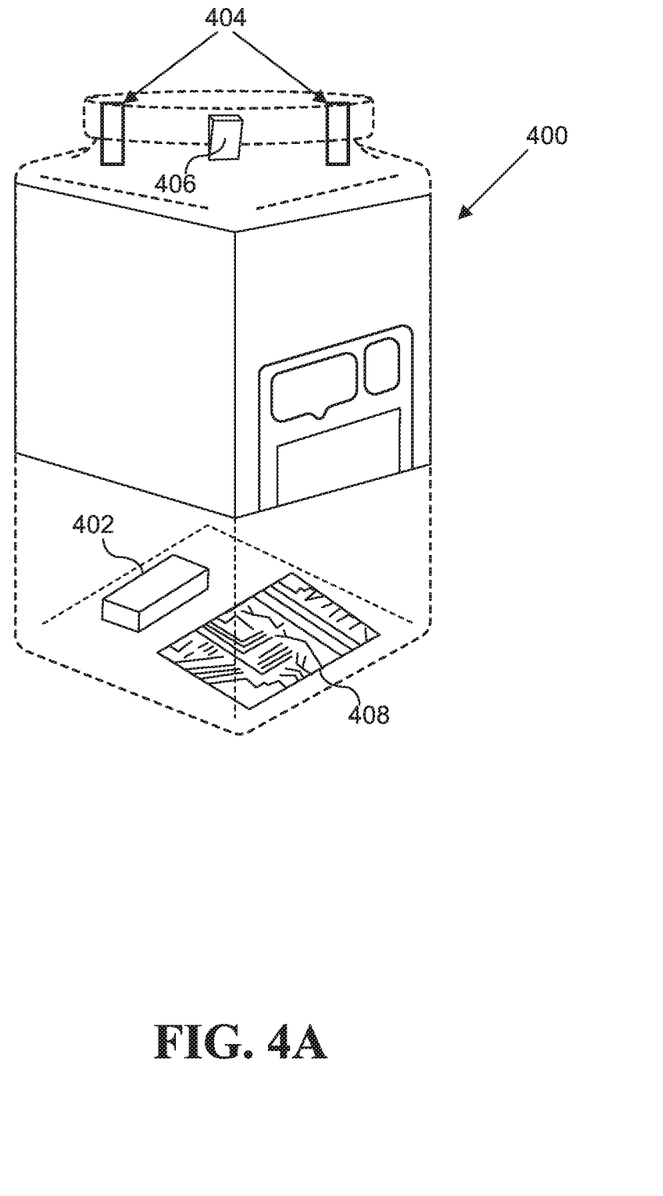
FIG. 4A is a partial cutaway view of a smart medication container in accordance with some embodiments.

FIG. 4A is a partial cutaway illustration of a smart medication container 400 in accordance with some embodiments. The smart medication container 400 includes a motion sensor 402, a pair of conductive elements 404, a lid sensor 406, and a communication module 408.

The motion sensor 402 generates motion sensor data represents movement of the container 400. Consequently, the motion sensor data can indicate when tilting, shaking, etc., occur as medication is dispensed from the smart medication container 400. The motion sensor 402 can also identify vibrations resulting from, for example, medication shifting in the container while being dispensed. Generally, the motion sensor 402 is a multi-axis (e.g., 4, 6) sensor capable of recognizing actions performed by the smart medication container 400. The motion sensor 402 may also be capable of receiving and installing over-the-air (OTA) firmware updates when the smart medication container includes a communication module 408.

The motion sensor data can be analyzed to determine physical movement or motion of the smart medication container 400. For example, movement experienced by the motion sensor 402 may cause an electronic display (e.g., electronic display 100 of FIG. 1) to illuminate. As another example, a motion sensor 402 can generate an acceleration vector from motion sensor data, which represents acceleration of the motion sensor 402 (and smart medication container 400) along the vector. The motion can be analyzed to determine whether it matches a distinctive motion associated with dispensing medication and, accordingly, whether medication was likely dispensed by the smart medication container 400. In some embodiments, the motion sensor data and/or associated motion(s) can be further analyzed to determine the amount or quantity of medication dispensed for a particular dose. For example, if the user inverts the smart medication container 400 twice, the user is likely to have dispensed two pills.

Contents of the smart medication container 400 are determined using at least one pair of conductive elements 404 that are placed substantially parallel to one another. These conductive elements 404 are also preferably positioned at or near the rim of the container. As medication leaves the container and travels between the conductive elements 404, the relative static permittivity of the area between the conductive elements changes and the subsequent change in capacitance is be measured. The changes in capacitance, and the capacitance measurements themselves, can then be used to determine whether medication was dispensed from the container and, if so, how much medication was dispensed.

More than one pair of conductive elements could also be placed within the opening of the container 400. In such embodiments, each pair of conductive elements 404 is configured to generate a separate capacitance measurement. When used together, these measurements are able to generate a more accurate measurement of the change in capacitance that is less susceptible to noise. For example, a smart medication container 400 having a rectangular opening could have two pairs of conductive plates along its side walls, while a container having a hexagonal opening could have three pairs of conductive plates. A pair of conductive elements 404 may also be placed along the top (e.g., bottom of the lid) and bottom of the smart medication container 400 that are configured to measure the amount of medication remaining in the container. In some embodiments, the smart medication container 400 includes multiple sections for holding different medications. In order to accurately measure the amount and/or quantity of medication remaining in each section, at least one pair of conductive elements 404 is positioned within each section. Together with at least the lid sensor 406 and communication module 408, the conductive elements 404 may allow medication to be automatically dispensed in proper doses and at the proper times.

For example, 4-sided, 6-sided, 8-sided, etc., smart medication containers 400 can measure capacitance using more than one pair of conductive elements positioned substantially parallel to one another along the sides of the container 400. Capacitance can be measured by two or more different pairs of conductive elements, and those measurements can be used in conjunction with one another to reduce error from noise, variations in content (e.g., medication) position, etc. One skilled in the art will recognize a 6-sided container could have up to three distinct pairs of conductive elements, an 8-sided container could have four distinct pairs, etc.

Figure 4B:
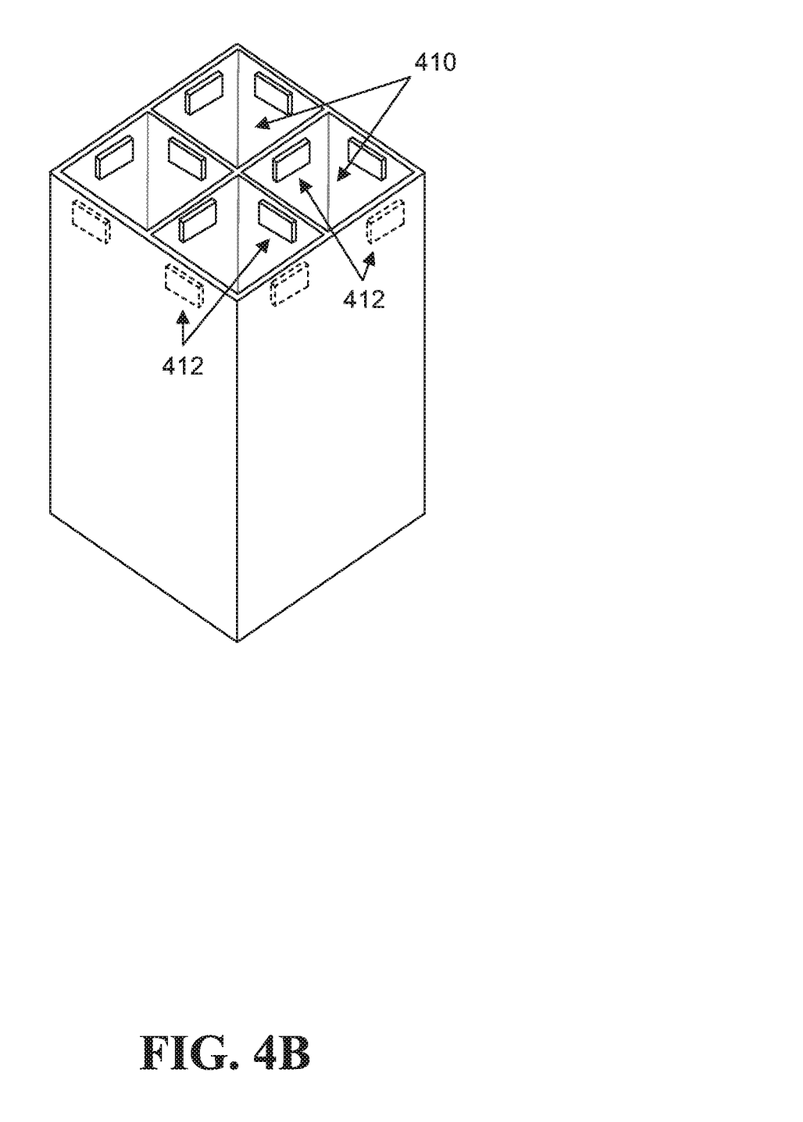
FIG. 4B is a perspective view of a smart medication container having multiple cells for storing medication.

As illustrated by FIG. 4B, the smart medication container 400 may also include multiple (e.g., 2, 4) cells 410 that can be used to store different medications or doses of medication. Capacitance can be measures between pairs of parallel walls so that the contents of each cell can be measured individually and independently. Each cell's contents could also be measured by multiple pairs of conductive elements 412 that are used in conjunction with one another to reduce error from noise, variations in content (e.g., medication) position, etc.

Sensor data can also be generated by a lid sensor 406 that determines whether the smart medication container 400 is open or closed. The lid sensor 406 may be, for example, an optical sensor oriented toward the opening of the smart medication container 400, a pressure sensor upon which pressure is exerted when the lid is on, etc. The communication module 408, meanwhile, is configured to establish a connection with one or more other computing devices. Examples of computing devices include mobile phones, tablets, portable media devices, wearable devices, laptops, servers, etc.

The connection allows information (e.g., measurements) recorded by the electronic display 102, audio sensor 202, user input(s) 302, ambient sensor(s) 304, motion sensor 402, conductive elements 404, lid sensor 406, etc., to be transmitted electronically across a network. Generally, the communication module 408 establishes a wireless communication link between the smart medication container 400 and the other intelligent device(s). For example, the smart medication container 400 may support Bluetooth, cellular (e.g., 3G, 4G), Bluetooth Low Energy (BLE), near field communication (NFC), wireless local area network (WLAN) transmitters (e.g., WiFi/IEEE 802.11 compliant transmitter), and/or other wireless technologies. The smart medication container 400 could, however, instead or also be configured to transfer sensor data via a wired connection (e.g., USB, mini-USB).

The communication module 408 can be housed within an electronics module compartment, which may also house additional modules and/or components (e.g., processors, communication devices, integrated electronics, memory storage devices, batteries, sensors). For example, in some embodiments the electronics module compartment includes a gesture recognition module that can be used to detect movement and position of the smart medication container 400.

One skilled in the art will recognize embodiments of the smart medication device can include some or all of the components described herein with respect to FIGS. 1-4. Some embodiments may, for example, include only an electronic display, while other examples include most or all of the aforementioned components. Moreover, some embodiments may include additional components not pictured or described herein that contribute to improving the likelihood an individual complies with a medication regimen.

Figure 5:
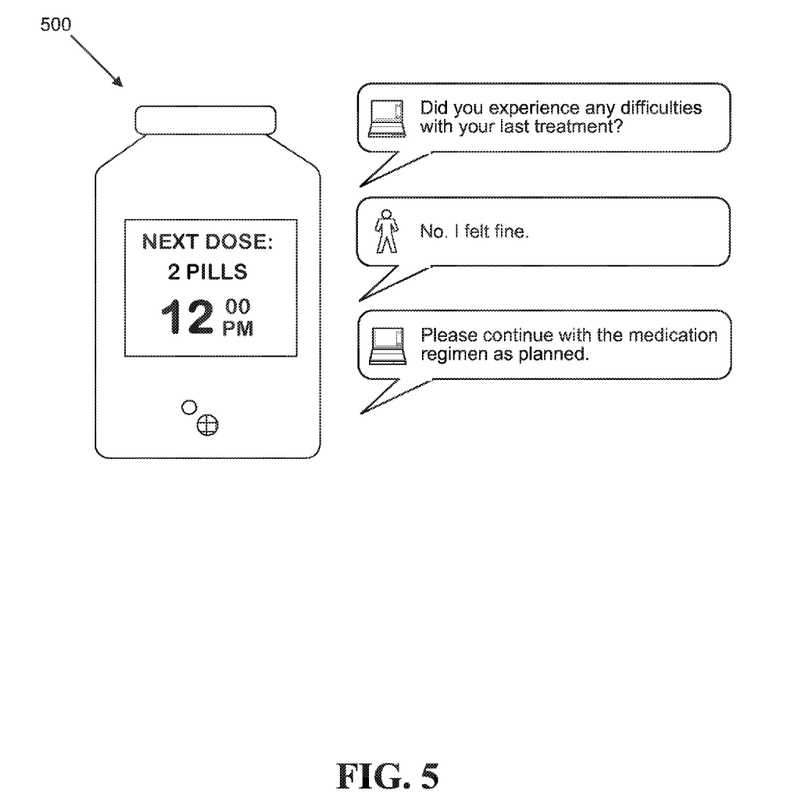
FIG. 5 depicts a sample conversational exchange as may occur when a smart medication container employs voice recognition techniques.

FIG. 5 depicts sample conversational exchanges as may occur when a smart medication container 500 employs voice recognition techniques and/or relays audible data between itself and a remote computing system. In some embodiments, the smart medication container 500 includes an audio sensor (e.g., microphone) and a speaker. The audio sensor is able to record audible conversational elements (e.g., responses, questions) given by the user. Voice/speech recognition can be used to translate the audible conversational elements into text and determine whether keywords, key phrases, etc., were spoken by the user. Particular modules (e.g., speech recognition module, analysis module) may be used to perform some or all of these steps. Thus, the smart medication container 500 is able to replicate conversational exchanges between the user and a medical professional (e.g., physician, pharmacist). In some embodiments, natural language processing (NLP) and/or machine learning (ML) techniques may be employed to improve the effectiveness of speech recognition, the selection of appropriate conversational elements, etc.

In some embodiments, the smart medication container 500 is completely or semi-autonomous (i.e., no human action is necessary) in determining what responses, inquiries, etc., are appropriate under the circumstances. In other embodiments, the smart medication container 500 allows a medical professional (e.g., physician, pharmacist) to provide feedback from a remote location. Consequently, audible supervision and instructions can be provided while the medication is being administered. The medical professional may be able to trigger content to be displayed on the electronic display, such as animations. Other forms of communication may also be supported. For instance, the electronic display may also allow the user and medical professional to exchange text-based messages, while a camera may allow the medical professional to visually supervise administration of the medication.

The user may be prompted to provide feedback before, during, or after administering medication. For example, the smart medication container 500 could begin a conversational exchange by posing a question ("Did you experience any difficulties with your last treatment?") and waiting for a response. Once an audible response ("No.") is received, the smart medication container 500 can perform vocal recognition. Recognized elements, such as letters, words, or phases, may cause the medication regimen to be modified. For example, certain keywords (e.g., answering "yes" to the question posed in FIG. 4) may indicate additional questions should be posed to the user, a medical professional should be contacted, etc. Key words and phrases could also reveal whether the medication regimen is successful and, accordingly, elements recognized within the user's response(s) may be used to modify the medication regimen itself.

Figure 6:
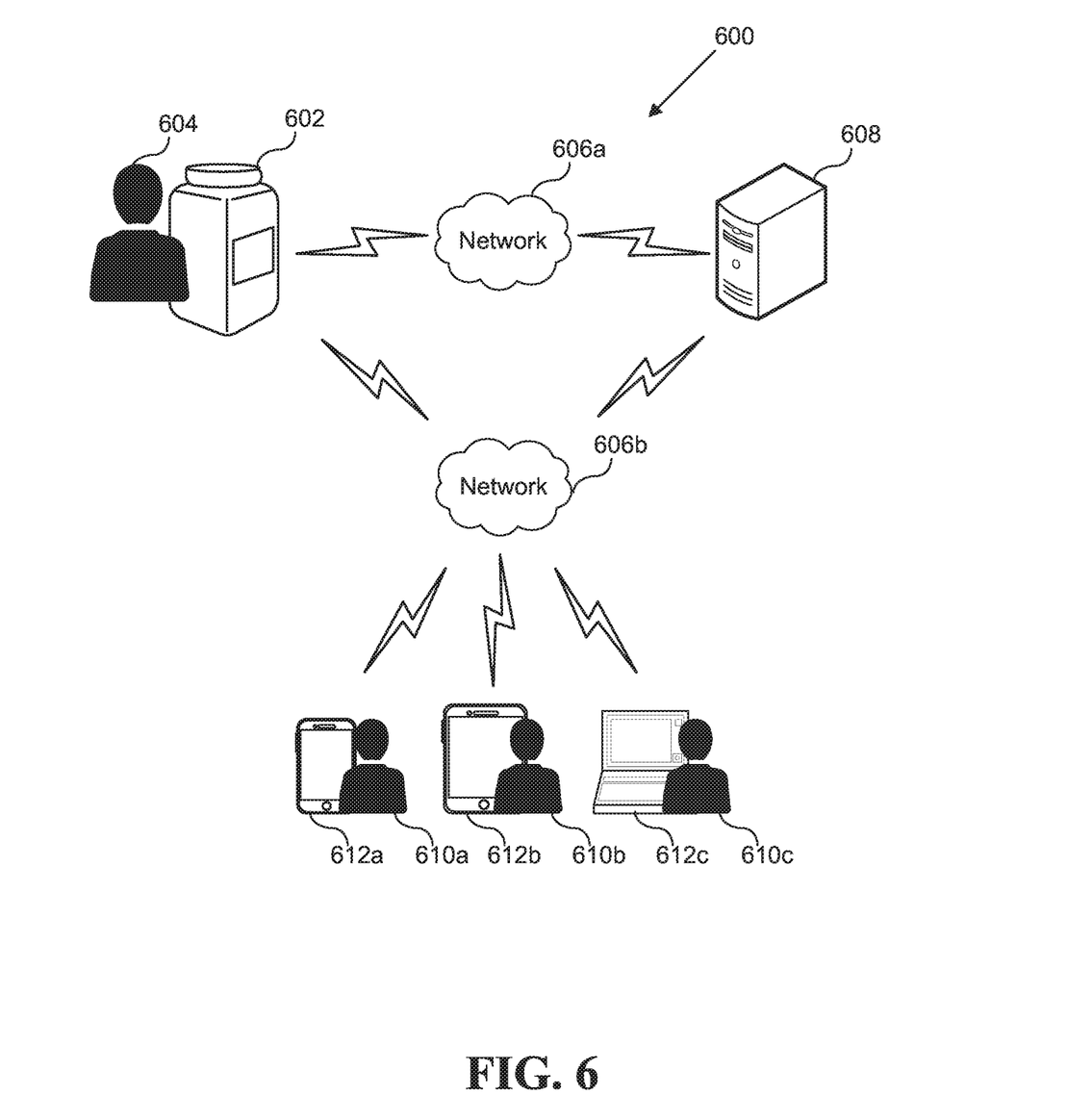
FIG. 6 is a generalized diagram depicting components of a system for monitoring administration of medication and adherence to a medication regimen.

FIG. 6 is a generalized block diagram depicting components of a system 600 for reviewing, monitoring, etc., the administration of medication in accordance with a medication regimen. In some embodiments, the smart medication container 602 is communicatively coupled to a distinct computing system 608 (e.g., server) over a network 606a, such as the Internet. The smart medication container 602 and/or distinct computing system 608 can perform some or all of the methods described herein. That is, the system 600 can be distributed amongst the smart medication container 602 and the distinct computing system 608.

In some embodiments, one or more network-accessible devices 612a-c that are controlled by family members, physicians, pharmacists, etc., 610a-c are communicatively coupled to the smart medication container 602, the distinct computing system 608, or both. One or more networks 606a-b can be used to communicatively couple the various components of the system 600. Network 606a can be the same as, or distinct from, network 606b.

Such a configuration allows physicians, pharmacists, administrators of a pharmaceutical trial, etc., 610a-c to supervise the user 604 while the medication is administered. While the smart medication container 602, distinct computing system 608, and network-accessible devices 612a-c are depicted as wirelessly communicating with one another, wired connections are also possible and, in some embodiments, may be preferred.

Figure 7:
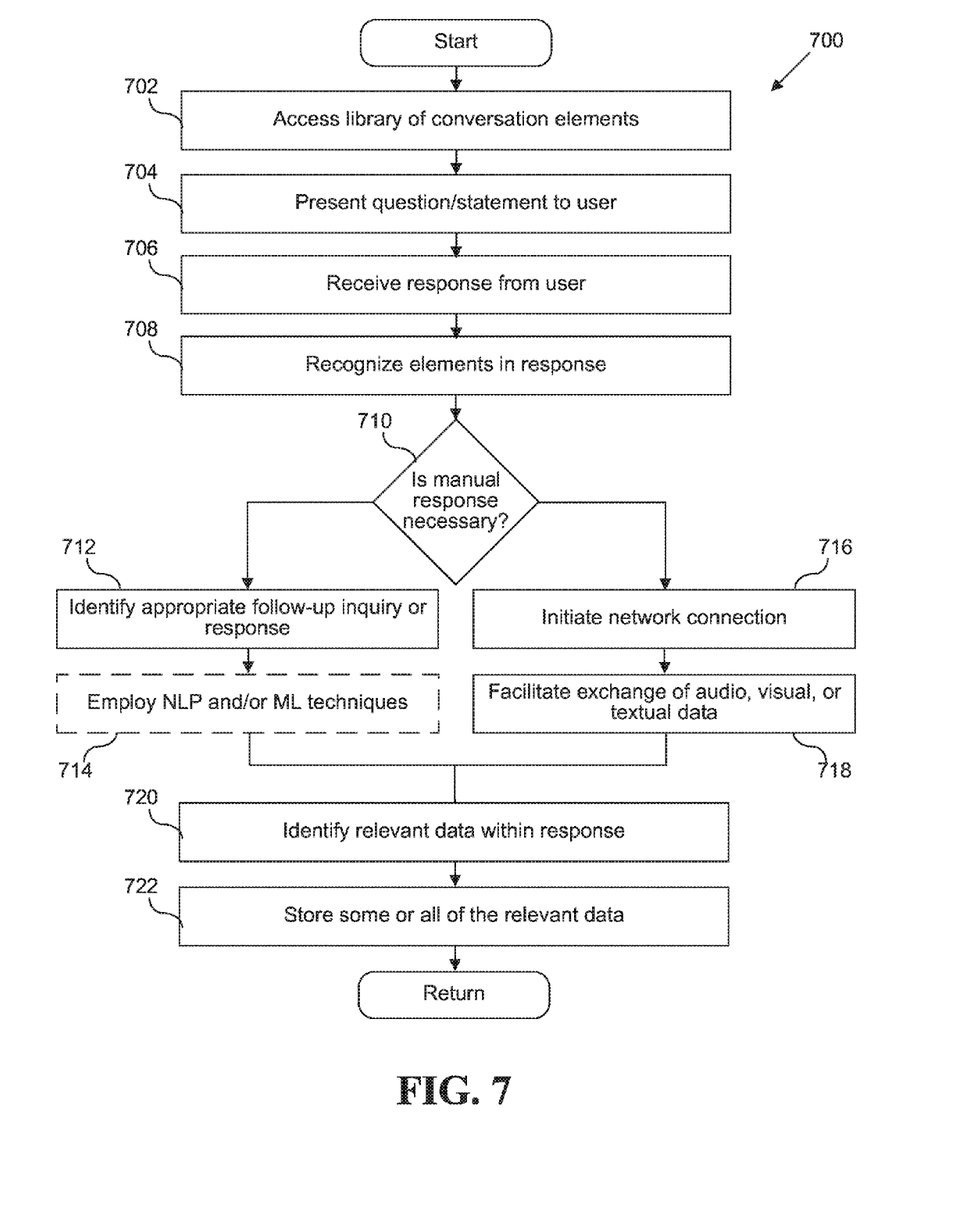
FIG. 7 is a flow diagram depicting a process for managing the administration of medication as may occur in various embodiments.

FIG. 7 is a flow diagram depicting a process 700 for administering medication and monitoring compliance with a medication regimen as may occur in various embodiments. At block 702, a smart medication container can access a library of conversation elements, such as inquiries and responses. In some embodiments, the library of conversation elements is stored locally (e.g., within a storage of the smart medication container), while in other embodiments the library of conversation elements is stored remotely (e.g., on a remote storage communicatively coupled to the smart medication container).

At block 704, the smart medication container presents a question, statement, etc., to a user that is intended to elicit a response. The question, statement, etc., may seek to elicit specific or general information from the user that can be used to determine compliance with a medication regimen, identify complications, modify subsequent dosages of medication, etc. For example, the smart medication container may ask, "Did you experience any issues after administering medication this morning?" Wrong or unexpected answers may be flagged for additional follow-up. At block 706, the smart medication container receives a response from the patient. Generally, the response is audible, although other methods of communication (e.g., text-based messages, visual gesture recognition) may also be used.

At block 708, the smart medication container recognizes elements within the response received from the user. Various embodiments can employ text, gesture, and/or speech recognition depending on how the user elects to respond. At block 710, the smart medication container can determine whether a manual response (e.g., from a physician or pharmacist) is necessary based on the recognized elements.

If a manual response is not necessary, the recognized elements (e.g., words, phrases) can be used to identify an appropriate follow-up inquiry or response, as shown at block 712. For example, if the speech recognition indicates the user described a problem after administering medication, the smart medication container may ask the user for additional information. In some embodiments, NLP and/or ML techniques are employed to improve recognition of keywords and phrases, as shown at block 714. The NLP and/or ML can be performed locally by the smart medication container, remotely by a distinct computing device (e.g., mobile phone, tablet, computer, server), or both.

However, if a manual response is determined to be necessary, the smart medication container can initiate a connection with at least one network-accessible computing device (e.g., mobile phone, tablet, computer) associated with a medical professional, as shown at block 716. The at least one network-accessible device may be the same as, or distinct from, the distinct computing device. At block 718, real-time communication is facilitated be relaying audible, visual, or textual messages between the smart medication container and the at least one network-accessible computing device. Thus, the smart medication container allows a medical professional to remotely supervise administration of the medication.

At block 720, the smart medication container and/or the distinct computing device identify relevant data within the response. The relevant data may be expected (e.g., recitation of name or phone number to confirm user identity) or unexpected (e.g., unprompted response describing a recent symptom). At block 722, some or all of the relevant data is stored by the smart medication container and/or the distinct computing device. The relevant data may be stored, for example, in a database entry corresponding to the user. In some instances, all relevant data is kept (e.g., an entire user response that indicates increased risk of dangerous side effects). In other instances, a subset or summary of the relevant data is kept (e.g., a notification the patient experienced no symptoms from previous round of treatment).

Figure 8:
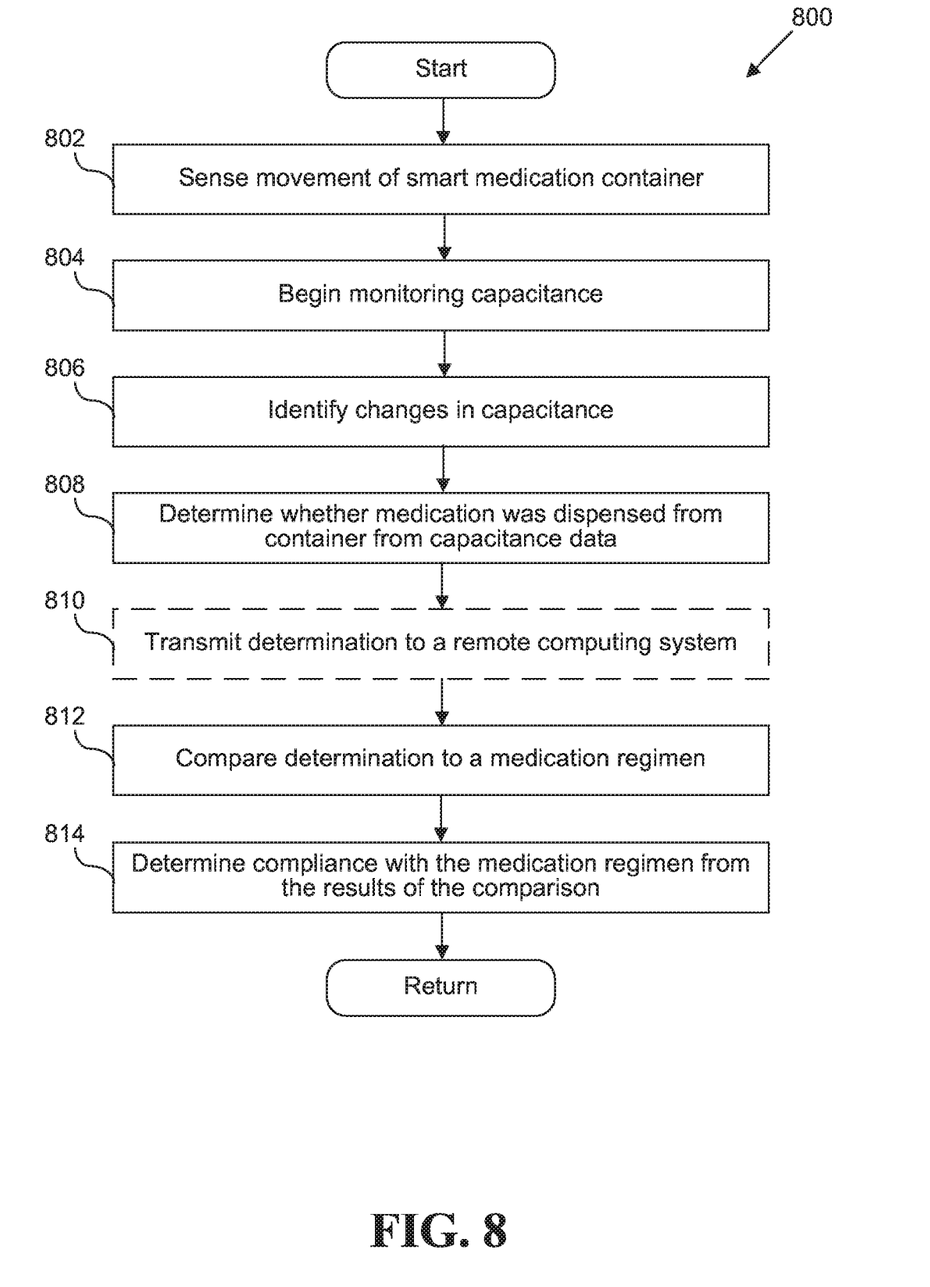
FIG. 8 is a flow diagram of a process for monitoring adherence to a medication regimen as may occur in some embodiments.

FIG. 8 is a flow diagram of a process 800 for monitoring adherence to a medication regimen as may occur in some embodiments. At block 802, the smart medication container senses movement (e.g., via a motion sensor) of the container. Additionally or alternatively, the smart medication container may turn on or "wake up" after receiving a user input from a tactile sensor or an electronic display, identifying an audible command, etc. At block 804, the smart medication container causes at least one pair of conductive elements to begin monitoring capacitance between the conductive elements. At block 806, the pair(s) of conductive elements identify changes in capacitance due to, for example, medication being dispensed from the smart medication container and passing between the conductive elements.

At block 808, the smart medication container or some other computing device determines whether medication was dispensed from the smart medication container from the capacitance data generated by the pair(s) of conductive elements. Generally, the conductive elements are placed on opposite sides of the opening of the smart medicine container. Accuracy could be improved by using more than one pair of conductive elements that help reduce the impact of noise. In some embodiments, the smart medication container transmits the determination of whether medication was dispensed to a remote computing device (e.g., for review/ analysis by a medical professional, family member, or administrator of a pharmaceutical trial), as shown at block 810. At block 812, the determination is compared to the user's medication regimen and, at block 814, compliance with the medication regimen is determined based on the results of the comparison. For example, if the medication regimen requires the user to administer medication at noon, a determination should have been made at or around noon that medication was dispensed from the smart medication container (i.e., the conductive elements identified a change in capacitance). In some embodiments, compliance results may be delivered to a family member of the user, a medical professional, administrator of a pharmaceutical trial, etc.

Computer System

Figure 9:
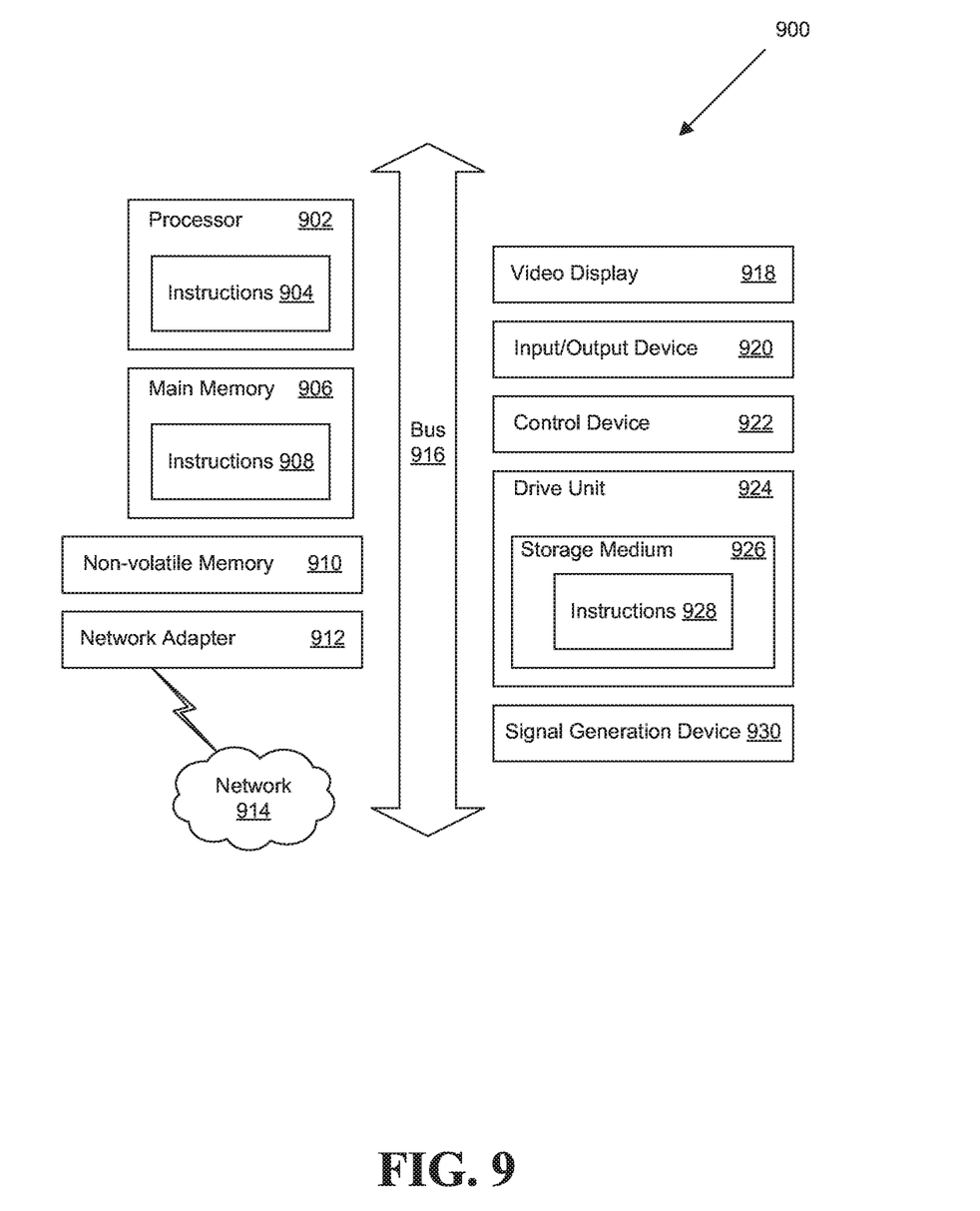
FIG. 9 is a block diagram illustrating an example of a computer system in which at least some operations described herein can be implemented according to various embodiments.

FIG. 9 is a block diagram illustrating an example of a computing system 900 in which at least some operations described herein can be implemented. The computing system may include one or more central processing units ("processors") 902, main memory 906, non-volatile memory 910, network adapter 912 (e.g., network interfaces), video display 918, input/output devices 920, control device 922 (e.g., keyboard and pointing devices), drive unit 924 including a storage medium 926, and signal generation device 930 that are communicatively connected to a bus 916. The bus 916 is illustrated as an abstraction that represents any one or more separate physical buses, point to point connections, or both connected by appropriate bridges, adapters, or controllers. The bus 916, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the computing system 900 operates as a standalone device, although the computing system 900 may be connected (e.g., wired or wirelessly) to other machines. In a networked deployment, the computing system 900 may operate in the capacity of a server or a client machine in a client-server network environment, or as a peer machine in a peer-to-peer (or distributed) network environment.

The computing system 900 may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the computing system.

While the main memory 906, non-volatile memory 910, and storage medium 926 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 928. The term "machine-readable medium" and "storage medium" shall also be taken to include any medium that is capable of storing, encoding, or carrying a set of instructions for execution by the computing system and that cause the computing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 904, 908, 928) set at various times in various memory and storage devices in a computer, and that, when read and executed by one or more processing units or processors 902, cause the computing system 900 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 910, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 912 enables the computing system 900 to mediate data in a network 914 with an entity that is external to the computing device 900, through any known and/or convenient communications protocol supported by the computing system 900 and the external entity. The network adapter 912 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 912 can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

Other network security functions can be performed or included in the functions of the firewall, can include, but are not limited to, intrusion-prevention, intrusion detection, next-generation firewall, personal firewall, etc.

As indicated above, the techniques introduced here implemented by, for example, programmable circuitry (e.g., one or more microprocessors), programmed with software and/ or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. A network-connected medication container for monitoring adherence to a medication regimen, the network-connected medication container comprising:
   a bottle configured to store medication pills,
      wherein the bottle includes an opening through which medication pills can be dispensed;
   a pair of conductive elements disposed within the opening of the bottle,
      wherein the pair of conductive elements are oriented substantially parallel to one another on opposing sides of the opening, and
      wherein the pair of conductive elements, when in use, generates capacitance data by continually measuring capacitance;
   a motion sensor fixedly attached to the bottle,
      wherein the motion sensor generates motion data indicative of movement of the bottle;
   a processor configured to
      examine the motion data generated by the motion sensor,
      detect an occurrence of a particular action,
      activate the pair of conductive elements responsive to detecting the occurrence of the particular action,
      identify changes in the capacitance data, and
      determine, based on the changes, whether a medication pill has passed between the pair of conductive elements and left the bottle;
   a wireless communication module configured to transmit the motion data generated by the motion sensor and the capacitance data generated by the pair of conductive elements to a remote computing device across a network; and
   a persistent electronic display that displays information associated with a medication regimen that requires administration of the medication pills.

2. A medication container comprising:
   a bottle that includes an opening through which medication can be dispensed;
   multiple pairs of conductive elements disposed within the opening of the bottle,
      wherein each pair of conductive elements are oriented substantially parallel to one another, and
      wherein each pair of conductive elements, when in use, generates capacitance data by continually measuring capacitance;
   a motion sensor fixedly attached to the bottle,
      wherein the motion sensor generates motion data indicative of movement of the bottle; and
   a processor configured to
      examine the motion data generated by the motion sensor,
      detect an occurrence of a particular action,
      activate at least one pair of conductive elements responsive to detecting the occurrence of the particular action, and
      identify changes in the capacitance data generated by the at least one pair of conductive elements that are caused by medication passing between the at least one pair of conductive element and leaving the bottle.

3. The medication container of claim 2, further comprising:
   a persistent electronic display able to display information associated with a medication regimen that requires administration of the medication;
   a lid sensor configured to determine whether a lid is positioned over the opening of the bottle; and
   a wireless communication module configured to transmit the motion data generated by the motion sensor, the capacitance data generated by the at least one pair of conductive elements, or both to a computing device.

4. The medication container of claim 2, wherein the medication container is chargeable via a wired connection, a wireless inductive connection, or both.

5. The medication container of claim 3, wherein the computing device is configured to:
   analyze the capacitance data recorded by the at least one pair of conductive elements to determine whether medication was dispensed from the bottle;
   analyze the capacitance data recorded by the at least one pair of conductive elements to determine whether contents within the bottle have changed and an amount by which the contents have changed;
   compare results of said analysis to the medication regimen; and determine whether a user is in compliance with the medication regimen.

6. The medication container of claim 2, further comprising:
an audio input device configured to
generate a recording by recording a statement made by a user while using the medication container, and
transmit the recording to a computing device using a wireless communication module.

7. The medication container of claim 2, further comprising:
an audio output device configured to
project a prerecorded audio recording, or
receive an audio recording via a wireless communication module and project the audio recording in real time.

8. The medication container of claim 2, further comprising at least one of a temperature sensor, a humidity sensor, or a pressure sensor.

9. The medication container of claim 2, further comprising:
one or more light-emitting diodes that visually convey information to a user.

10. The medication container of claim 2, further comprising:
one or more speakers that audibly convey information to a user.

11. A method for monitoring adherence to a medication regimen, the method comprising:
monitoring, by a motion sensor of a network-connected medication container, movement of the network-connected medication container;
detecting, by a processor of the network-connected medication container, an occurrence of a particular action;
in response to said detecting,
activating, by the processor of the network-connected medication container, a pair of conductive elements,
wherein the pair of conductive elements are disposed within an opening of the network-connected medication container through which medication is dispensed;
generating, by the pair of conductive elements of the network-connected medication container, capacitance data by continually measuring capacitance;
identifying, by the processor of the network-connected medication container, changes in the capacitance data that are indicative of dispersals of medication from the network-connected medication container;
transmitting, by a wireless communication module of the network-connected medication container, the capacitance data to a remote computing system;
determining, by the processor of the network-connected medication container, a compliance status that specifies whether the medication was dispensed from the network-connected medication container in compliance with a medication regimen; and
displaying, by an electronic display of the network-connected medication container, an indication of the compliance status as determined by the processor.

12. The method of claim 11, wherein the pair of conductive elements is one of a plurality of pairs of conductive elements positioned within the opening of the network-connected medication container and/or within a container wall surrounding contents of the network-connected medication container.

13. The method of claim 11, further comprising:
transmitting, by the wireless communication module of the network-connected medication container, the compliance status to a computing device for review by an individual.

14. A method for monitoring adherence to a medication regimen, the method comprising:
monitoring, by a motion sensor of a medication container, movement of the medication container;
detecting, by a first processor of the medication container, an occurrence of a particular action;
activating, by the first processor of the medication container, a pair of conductive elements,
wherein the pair of conductive elements are disposed within an opening of the medication container through which medication is dispensed;
generating, by the pair of conductive elements of the medication container, capacitance data by continually measuring capacitance between the pair of conductive elements;
identifying, by the first processor of the medication container, changes in the capacitance data;
transmitting, by a wireless communication module of the medication container, the capacitance data to a remote computing system;
determining, by a second processor of the remote computing system, whether medication has been dispensed from the medication container based on the changes, the capacitance data, or both;
comparing, by the second processor of the remote computing system, a determination as to whether medication was dispensed from the medication container with an administration schedule associated with a medication regimen; and
determining, by the second processor of the remote computing system, a compliance status based on the comparison.

15. The method of claim 14, wherein the pair of conductive elements is one of a plurality of pairs of conductive elements positioned within the opening of the medication container and/or within a container wall surrounding contents of the medication container.

16. The method of claim 14, further comprising:
transmitting, by the remote computing system, the compliance status to a computing device for review by an individual.

17. The method of claim 16, wherein the individual is a subject required to administer the medication in accordance with the medication regimen or a medical professional.

* * * * *